United States Patent [19]

Lee et al.

[11] Patent Number: 5,204,308
[45] Date of Patent: Apr. 20, 1993

[54] ANIONICALY STABILIZED LITHIUM CATALYSTS AND A METHOD FOR STABILIZING THE LITHIUM CATALYST

[75] Inventors: Anthony L. Lee, Glen Ellyn; Erek J. Erekson, La Grange; James T. Semrau, Chicago; S. Peter Barone, Hoffman Estates; Irving J. Solomon, Highland Park, all of Ill.

[73] Assignee: Institute of Gas Technology, Chicago, Ill.

[21] Appl. No.: 681,958

[22] Filed: Apr. 8, 1991

[51] Int. Cl.$^5$ .................. B01J 21/02; B01J 21/06; B01J 23/04; B01J 27/18
[52] U.S. Cl. .................. 502/208; 502/218; 502/241; 502/242; 502/243; 502/302; 502/303; 502/342; 502/344
[58] Field of Search ............ 502/208, 218, 243, 344, 502/241, 242, 302, 303, 342

[56] References Cited

U.S. PATENT DOCUMENTS

| | | | |
|---|---|---|---|
| 3,325,245 | 6/1967 | Rowton | 502/208 X |
| 3,751,496 | 8/1973 | Todo et al. | 502/208 X |
| 3,875,079 | 4/1975 | Witt | 502/243 X |
| 4,540,509 | 9/1985 | Burba | 502/344 X |
| 4,720,598 | 1/1988 | Scholte | 502/208 X |
| 4,902,661 | 2/1990 | Immel et al. | 502/218 X |
| 4,950,830 | 8/1990 | Erekson et al. | 585/444 |

FOREIGN PATENT DOCUMENTS 122025 10/1984 European Pat. Off. .

OTHER PUBLICATIONS

Chemical Abstracts, vol. 107, 43152w (1987).
The Condensed Chemical Dictionary, Sixth Edition, 1961, pp. 673, 674, 676, 677.
Kimble, J. B. and Kolts, J. H., Oxidative Coupling of Methane to Higher Hydrocarbons, Energy Progress, vol. 6, No. 4, p. 226 (1986).

Primary Examiner—W. J. Shine
Attorney, Agent, or Firm—Speckman & Pauley

[57] ABSTRACT

An anionically stabilized lithium catalyst wherein the anion is sulfate, phosphate, aluminate, silicate and mixtures thereof. The anionically stabilized lithium catalyst may be supported on a metal oxide support of magnesium oxide, titanium oxide, zinc oxide, calcium oxide, barium oxide, strontium oxide, zirconium oxide, hafnium oxide, yttrium oxide, lanthanum oxide, samarium oxide, and mixtures thereof or when aluminate or silicate is used as the anion the aluminate or silicate may act as the support. The catalyst may be used to promote reactions at temperatures higher than prior lithium catalysts, particularly higher than about 600° C., such as oxidative coupling of aliphatic and alicyclic hydrocarbons to produce higher molecular weight compounds and oxydehydrogenation of aliphatic and alicyclic hydrocarbons to produce unsaturated hydrocarbons or to change the functional group of the hydrocarbon.

6 Claims, 1 Drawing Sheet

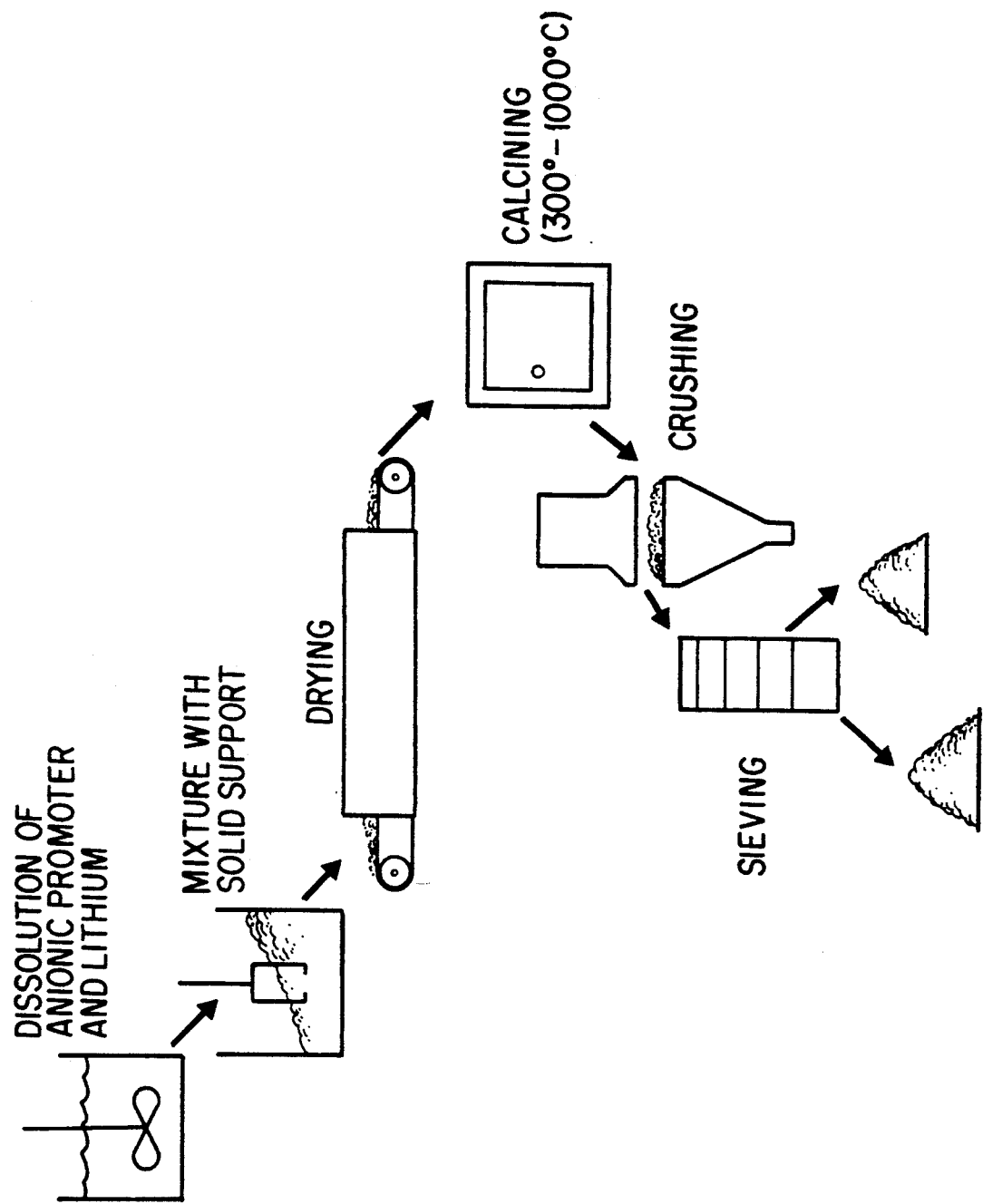

ANIONICALY STABILIZED LITHIUM CATALYSTS AND A METHOD FOR STABILIZING THE LITHIUM CATALYST

BACKGROUND OF THE INVENTION

1. Field of the Invention

This invention relates to stabilization of catalysts which normally become unstable at elevated temperatures of desired catalytic reactions. The invention promotes long term stabilization of lithium catalysts at reaction temperatures above about 600° C. to obtain higher conversion in reactions such as catalytic oxidative coupling of hydrocarbons to produce higher molecular weight compounds and oxydehydrogenation to produce unsaturated hydrocarbon compounds.

2. Description of Related Art

Use of lithium on basic metal oxides to catalyze chemical reactions such as oxidative coupling of aliphatic hydrocarbons to produce higher molecular weight products is known. J. B. Kimble and J. H. Kolts, Oxidative Coupling of Methane to Higher Hydrocarbons, Energy Progress, Vol. 6, No. 4, pp 226 (1986). Oxidative dehydrogenation of aliphatic hydrocarbons to form unsaturated hydrocarbon chains using lithium basic metal oxide catalysts is known. U.S. Pat. No. 4,950,830. When large amounts, over about 1 weight percent, lithium has been added to the basic oxides, lithium has had a tendency to vaporize and leave the catalyst/support at temperatures higher than about 600° C. thereby reducing the activity of the catalyst. J. B. Kimble et al., supra. Therefore, there is a need for a thermal stabilizer for lithium catalysts to preserve their activity when used to catalyze chemical reactions at temperatures higher than about 600° C.

SUMMARY OF THE INVENTION

It is an object of this invention to provide a stabilized lithium/oxide catalyst.

Another object of this invention is to provide a stable lithium catalyst for catalysis of chemical reactions conducted at temperatures higher than about 600° C.

A further object of this invention is to provide a process using a stable lithium/oxide catalyst for oxidative coupling of aliphatic hydrocarbons to produce higher molecular weight hydrocarbon compounds.

Another object of this invention is to provide a process using a stable lithium/oxide catalyst for oxydehydrogenation of hydrocarbon compounds to produce unsaturated compounds and for modification of a functional group.

These and other objects and advantages of the invention will become apparent upon description of preferred embodiments and specific examples.

These objects and advantages of the invention may be obtained by adding a stabilizing anion to the lithium catalyst. It is desired that the anionic stabilizer be combined with the lithium in an amount approximately stoichiometric to the corresponding lithium-anion compound. A lithium compound is probably formed, but some lithium may not form a compound and excess lithium is desired. Suitable anions for stabilization of the lithium according to this invention are selected from the group consisting of sulfate, phosphate, aluminate, silicate and mixtures thereof. The anionically stabilized lithium is loaded onto an oxide support in an amount of about 1 to about 20 weight percent active lithium, preferably about 5 to about 15 weight percent active lithium, based upon the total weight of the stabilized catalyst-support. Suitable oxide support materials for use in this invention are selected from the group consisting of magnesium oxide, titanium oxide, zinc oxide, calcium oxide, barium oxide, strontium oxide, zirconium oxide, hafnium oxide, yttrium oxide, lanthanum oxide, samarium oxide, and mixtures thereof. The stabilized lithium in the form of aluminate, silicate and mixtures thereof may be used directly in that form with the aluminate and/or silicate acting as support material. The anionically stabilized lithium catalysts of this invention have been found to increase conversion of methane to ethane and ethylene about three to four times that of the conversion using non-stabilized lithium catalyst at about 800° C.

BRIEF DESCRIPTION OF THE DRAWING

The Figure schematically shows preparation of a catalyst of this invention by one preferred method.

DESCRIPTION OF PREFERRED EMBODIMENTS

The catalyst of this invention is an anionically stabilized lithium. Suitable anions for stabilizing lithium according to this invention include sulphate, phosphate, aluminate, silicate and mixtures thereof. Sulphate is a preferred anion since the nominal compound formed is $Li_2SO_4$ having a melting point of about 880° C., a Li/anion ratio of 2 and provides about 12.6 weight percent lithium. For use at lower reaction temperatures, phosphate may be desirable since it provides a Li/anion ratio of 3 and about 18 weight percent lithium, but has a melting point of about 837° C. For use at higher temperatures, silicate is a preferred anion since it provides a Li/anion ratio of 2 and about 15.4 weight percent lithium while having a melting point about 1204° C. Aluminate may be used as an anion for use at higher temperatures since it has a melting point about 1625° C., provides a Li/anion ratio of 1 and 10.5 weight percent lithium.

The anionically stabilized lithium may be used on an oxide support. Suitable oxide support materials include magnesium oxide, titanium oxide, zinc oxide, calcium oxide, barium oxide, strontium oxide, zirconium oxide, hafnium oxide, yttrium oxide, lanthanum oxide, samarium oxide, and mixtures thereof. Magnesium oxide is a preferred support material. The anionically stabilized lithium may be loaded onto the support material in an amount of about 1 to about 20 weight percent lithium based upon the total weight of the stabilized catalyst-support. Preferred loading of stabilized lithium is about 5 to about 15 weight percent lithium based upon the total weight of the stabilized catalyst-support. When aluminate and/or silicate is used as the stabilizing anion, the aluminate and/or silicate itself may act as the catalyst support material or the aluminate and/or silicate may be loaded onto the oxide support material.

The anionically stabilized catalysts according to this invention may be formed by forming a lithium/anion compound wherein the anion is selected from sulfate, phosphate, aluminate, silicate and mixtures thereof. Excess lithium is desired. Any method for forming such compound may be used. A preferred method is to dissolve a soluble lithium compound, such as lithium hydroxide or lithium nitrate, and a soluble compound of an anion of the above group such as ammonium sulfate, sulfuric acid, phosphoric acid, aluminum nitrate, silicic acid, and lithium salts of the anions, such as lithium sulfate, lithium phosphate, and lithium silicate in water with stirring to dissolve. Heating of the solution may be desirable to aid in solution. The anionically stabilized lithium may be loaded onto the oxide support by any method known to the art for such catalyst loading. One preferred method is to pour the anionically stabilized lithium solution over the oxide support with stirring followed by removal of the excess liquid. The dried anionically stabilized lithium on the oxide support is then heated to about 300° to about 1,000° C., preferably about 600° to about 900° C. for about ½ hour to about 4 hours preferably about ½ to about 1 hour to bond the lithium/anionic materials to the support. Calcining is also performed to heat the catalyst to temperatures higher than process temperatures to be certain that no volatile compounds are formed and that no phase transformations occur after the catalyst is loaded into the reactor for conduct of the catalytic process. The solid product of anionically stabilized lithium on the oxide support, including the aluminate or silicate, may be crushed and sieved to small size for catalytic use. The Figure schematically shows the above described process for production of a catalyst according to this invention. Conventional and well known catalyst manufacturing techniques may be employed to produce the supported catalyst described above. When preparing these catalytic materials, it is preferred to employ manufacturing techniques resulting in a product having a substantially uniform or homogeneous composition. Shaping of the material may be effected according to conventional techniques of the art, particularly tableting, pelleting or extrusion.

The catalyst of this invention provides an active lithium catalyst which is thermally stable at higher reaction temperatures than prior lithium catalysts. The catalyst of this invention may be used in catalytic reaction up to about 20 degrees Centigrade below the melting point temperature of the particular catalyst used. As pointed out above, the melting points of the anionically stabilized catalysts of this invention are higher than about 800° C. and up to higher than about 1600° C. Therefore, the anionically stabilized catalysts of this invention may be used and maintain stability at temperatures higher than prior used lithium catalysts. The catalysts of this invention are suitable for use in any lithium catalyzed reaction, particularly those which benefit from reaction temperatures of over about 600° C.

One advantageous lithium catalyzed reaction according to this invention is gas phase oxidative coupling of hydrocarbons to produce higher molecular weight hydrocarbons by lengthening the hydrocarbon chain. Suitable feedstocks for use in this reaction include aliphatic and alicyclic hydrocarbon compounds including aliphatic and alicyclic substituted aromatic hydrocarbon compounds. Suitable aliphatic and alicyclic hydrocarbon compounds for use as feedstocks include straight and branched chain saturated and unsaturated aliphatic hydrocarbons, such as, methane, ethane, propane, butane, heptane, pentane, hexane, octane, isobutane, isohexane, isooctane, 1-pentene, 1-hexene, and mixtures thereof; cyclic chain saturated and unsaturated alicyclic hydrocarbons, such as, cyclobutane, cycloheptane, cyclohexane, cyclohexene and mixtures thereof; and aryl substituted aliphatic and alicyclic hydrocarbons, such as, toluene, xylene, indan, tetralin, mesitylene, durene, cumene and mixtures thereof. By the terminology "aliphatic and alicyclic hydrocarbon compounds" we mean to include substituted aromatic hydrocarbon compounds having an aromatic ring with at least one aliphatic or alicyclic hydrocarbon radical substituent on the aromatic ring. In the case of unsaturated hydrocarbons, it should be noted that the oxidative coupling of this invention does not occur at the unsaturated bonding.

In one embodiment gas phase oxidative coupling of methane by reaction of methane and oxygen in the presence of the above identified anionically stabilized lithium catalyst produces higher molecular weight hydrocarbons, predominantly ethane and ethylene. Feedstock gas comprising methane suitable for use in this embodiment may comprise any methane containing gas which does not contain interfering compounds. Preferably, the methane containing gas comprises about 25 mole percent up to about 100 mole percent methane. Suitable sources for methane containing gas include natural gas, synthetic natural gas (SNG), product gas from gasification of carbonaceous materials, such as gasification of coal, peat, shale, and the like, as well as products of anaerobic digestion of various biomass materials. These gases principally comprise methane and may contain other hydrocarbon gases such as ethane and propane which may produce corresponding chemical reactions to those of methane in the process of this embodiment. Purification of such mixed gases comprising principally methane is not usually necessary. These sources of methane containing gas and processes for producing methane are well known to the art.

Another important oxidative coupling reaction according to the process of this invention is the production of styrene directly by coupling of toluene and methane by the following reaction in the presence of the above defined catalyst:

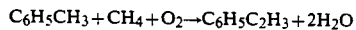

$$C_6H_5CH_3 + CH_4 + O_2 \rightarrow C_6H_5C_2H_3 + 2H_2O$$

At 750° C. the heat of reaction ($\Delta H$) is $-73$ kcal/mole and the sensible heat plus the heat of vaporization of toluene is about 55 kcal/mole. Thus the process operates close to autothermal conditions after initial light-off. Conventional processes using $Fe_2O_3$ as a catalyst with $Cr_2O_3$ as a stabilizer and $K_2CO_3$ as a coke retardant for production of styrene require ethylbenzene feedstock, produced from expensive benzene and ethylene and require large amounts of superheated steam (800° C. and molar ratio 14 steam to 1 ethylbenzene) due to the conversion of ethylbenzene to styrene being endothermic. The process of this invention uses relatively inexpensive toluene, methane and air as feedstock to a single reactor where both styrene and ethylbenzene are produced in a process that does not require superheated steam.

Any oxygen containing gas not containing interfering chemical compounds is useful as a feedstock in the process according to this invention. The term "oxygen containing gas" as used throughout this disclosure and claims refers to gas containing oxygen, such as air and gases having an oxygen content up to about 100 percent. It is preferred to use oxygen containing gas comprising over about 50 volume percent oxygen. The mole percentage oxygen relative to the aliphatic or alicyclic hydrocarbon in the process of this invention is about 2 to about 40 and preferably about 5 to about 20 mole percent oxygen.

The catalyst may be placed into a reactor, such as a tube-shell fixed bed, fluidized bed, moving bed, interbed heat exchange type, Fischer-Tropsch type, or other reactor type known to the art. Suitable reactor vessels for use at the desired operating temperatures and pressures are well known to the art. The oxidative coupling reaction of this invention is carried out by passing a gaseous mixture comprising aliphatic and/or alicyclic hydrocarbon and oxygen over the anionically stabilized lithium catalyst of this invention at about 600° C. to about 1,000° C., preferably about 700° C. to about 900° C. Suitable gas residence times are about 0.00002 to about 0.002 hour, preferably about 0.0001 to about 0.0005 hour. The reaction may be carried out at pressures of about 1 to about 1515 psia, preferably about 1 to about 150 psia.

The reactants may be fed to the catalytic reaction zone in proportions of about 10 mole percent to about 90 mole percent aliphatic and/or alicyclic hydrocarbon compounds, preferably about 50 to about 70 mole percent, and about 5 to about 30 mole percent oxygen, preferably about 8 to about 15 mole percent. Steam may be added in an amount up to about 1 mole steam per mole hydrocarbon to inhibit deep oxidation. Steam does not enter into the reaction, but solely acts as an oxidation inhibitor. The amounts of oxygen used are expressed as pure oxygen. The oxygen containing gas may be preheated by thermal exchange with the catalyst bed to a temperature suitable for the reaction controlling step of this process.

In another embodiment of this invention the anionically stabilized lithium catalyst may be used to promote oxydehydrogenation of aliphatic and alicyclic compounds as identified above to form unsaturated hydrocarbon chains, such as oxydehydrogenation of n-butane to form n-butene and water at about 600° to about 800° C. and 1 atmosphere pressure.

In still another embodiment, the anionically stabilized lithium catalyst may be used to promote oxydehydrogenation for modification of a functional group of aliphatic and alicyclic compounds as identified above, such as oxydehydrogenation of an alcohol to form a ketone or aldehyde, such as isopropyl alcohol to form acetone and water at about 100° to about 500° C. and 1 atmosphere pressure.

The following examples are set forth using specific materials and specific reaction conditions for detailed exemplification of the invention and should not be considered to limit the invention in any way.

EXAMPLE I

An anionically stabilized lithium catalyst on magnesium oxide was prepared by dissolving 54.69 grams of LiOH-H$_2$O (Fisher Lot #861075) and 85.25 grams of (NH$_4$)$_2$SO$_4$ (Baker Lot #38008) in 240 grams of deionized water with stirring until all of the chemical was dissolved. The solution of lithium and sulfate was poured over 90.05 grams of MgO (Alfa Lot #HO2H) with stirring. The lithium sulfate solution—MgO was heated on a hot plate for ½ hour with stirring to remove excess water and then dried overnight in an oven at 109° C. After drying, the material was transferred to a crucible and heated to 801° C. in air for ½ hour and allowed to cool slowly. The molar ratio of lithium/sulfate was 2.02 and the weight percent of lithium in the total catalyst material was about 10 percent. The solid product was a sulfate stabilized lithium on magnesium oxide carrier suitable for use as a catalyst.

EXAMPLES II

Sulfate stabilized lithium catalyst on magnesium oxide as prepared in Example I was ground into granules and sieved to −8+20 mesh. Twelve grams of such granules was packed into a laboratory sized tubular reactor. Feed to one end of the reactor was 600 cc/minute methane and 400 cc/minute air and the reactor was maintained at 800° C. Product gas was withdrawn from the opposite end of the reactor and analyzed for CO$_2$, CO, C$_2$H$_6$, C$_2$H$_4$, CH$_4$, O$_2$ and N$_2$ and conversion of methane to all products was 18.8 percent while selectivity of methane to ethane and ethylene was 78.5 percent.

EXAMPLE III

An anionically stabilized lithium catalyst on magnesium oxide was prepared by adding 16.66 grams of Li$_3$PO$_4$ (Alfa Lot #H16H) powder to 52.2 grams of deionized water with stirring to make a slurry suspension, due to the low solubility of Li$_3$PO$_4$. The lithium phosphate suspension was poured over 30.01 grams of MgO (Alfa Lot #HO2H) with stirring. The lithium phosphate suspension—MgO was then dried overnight in an oven at 109° C. After drying, the material was transferred to a crucible and heated to 801° C. in air for ½ hour and allowed to cool slowly. The molar ratio of lithium/phosphate was 3.0 and the weight percent of lithium in the total catalyst material was about 10 percent. The solid product was a phosphate stabilized lithium on magnesium oxide carrier suitable for use as a catalyst.

EXAMPLE IV

Phosphate stabilized lithium catalyst on magnesium oxide as prepared in Example III was ground into granules and sieved to −8+20 mesh. Oxidative coupling of methane was carried out in a tubular reactor as described in Example II except the temperature was maintained at 803° C. Conversion of methane to all products was 20.8 percent while selectivity to ethane and ethylene was 67.1 percent.

EXAMPLE V

Comparative Example

A non stabilized catalyst of lithium on magnesium oxide having a lithium/magnesium oxide weight ratio of 1/10 was used in oxidative coupling of methane in the same manner as described for Examples II and IV with the temperature maintained at 800° C. resulting in 5.2 percent methane conversion and selectivity to ethane and ethylene of 76.8 percent.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of the invention.

We claim:

1. An anionically stabilized lithium catalyst comprising lithium stabilized with an anion selected from the group consisting of phosphate, aluminate, silicate and mixtures thereof, said stabilized lithium supported on a metal oxide support selected from the group consisting of magnesium oxide, titanium oxide, zinc oxide, calcium oxide, barium oxide, strontium oxide, zirconium oxide, hafnium oxide, yttrium oxide, lanthanum oxide, samarium oxide and mixtures thereof.

2. An anionically stabilized lithium catalyst according to claim 1, wherein said lithium is present in an amount of about 1 to about 20 weight percent, based upon the total weight of the supported catalyst.

3. An anionically stabilized lithium catalyst according to claim 1 wherein said anion is phosphate and the phosphate stabilized lithium is on magnesium oxide support, said lithium comprising about 5 to about 15 weight percent, based upon the total weight of the supported catalyst.

4. A method for stabilizing lithium for use as a catalyst above about 600° C. comprising forming a lithium-/anion compound on a metal oxide support wherein said anion is selected from the group consisting of phosphate, aluminate, silicate and mixtures thereof.

5. A method for stabilizing lithium for use as a catalyst according to claim 4 wherein said lithium is present in an amount of about 1 to about 20 weight percent, based upon the total weight of the supported catalyst.

6. A method for stabilizing lithium for use as a catalyst according to claim 4 wherein said anion is phsophate and the phosphate stabilized lithium is on magnesium oxide support, said lithium comprising about 5 to about 15 weight percent, based upon the total weight of the supported catalyst.

* * * * *